(12) United States Patent
Ivanov et al.

(10) Patent No.: US 7,934,869 B2
(45) Date of Patent: May 3, 2011

(54) POSITIONING AN OBJECT BASED ON ALIGNED IMAGES OF THE OBJECT

(75) Inventors: Yuri A. Ivanov, Arlington, MA (US); John C. Barnwell, III, Leominster, MA (US); Andrea E. G. Bradshaw, North Brunswick, NJ (US)

(73) Assignee: Mitsubishi Electric Research Labs, Inc., Cambridge, MA (US)

( * ) Notice: Subject to any disclaimer, the term of this patent is extended or adjusted under 35 U.S.C. 154(b) by 81 days.

(21) Appl. No.: 12/495,744

(22) Filed: Jun. 30, 2009

(65) Prior Publication Data

US 2010/0329432 A1    Dec. 30, 2010

(51) Int. Cl.
*A61B 6/08* (2006.01)
*H05G 1/08* (2006.01)
*A61N 5/10* (2006.01)

(52) U.S. Cl. ............... 378/205; 378/20; 378/65; 378/91; 378/204; 600/407; 600/425

(58) Field of Classification Search .................... 378/20, 378/62, 65, 91, 95, 196, 197, 204, 205; 600/407, 600/425, 427
See application file for complete search history.

(56) References Cited

U.S. PATENT DOCUMENTS

| | | | | |
|---|---|---|---|---|
| 5,901,199 A | * | 5/1999 | Murphy et al. | 378/65 |
| 6,463,121 B1 | * | 10/2002 | Milnes | 378/62 |
| 6,516,046 B1 | * | 2/2003 | Frohlich et al. | 378/65 |
| 6,530,688 B1 | * | 3/2003 | Muller | 378/197 |
| 7,204,640 B2 | * | 4/2007 | Fu et al. | 378/205 |

OTHER PUBLICATIONS

Vincent Hayward et al., "Kinematic Decoupling in Mechanisms and Application to a Passive Hand Controller Design," Journal of Robotic Systems 10(5), 767-790 (1993).*

* cited by examiner

*Primary Examiner* — Allen C. Ho
(74) *Attorney, Agent, or Firm* — Dirk Brinkman; Gene Vinokur (57) ABSTRACT

Embodiment of the invention describes a system and a method for positioning an object from a first pose to a second pose. The method displays concurrently a first image and a second image on a display device, wherein the first image and the second image represent respectively the first pose and the second pose of the object. The method updates, in response to a change in a pose of the display device, the second image such that an alignment of the first image and the second image on the display device depends on the change in the pose of the display device, and positions the object from the first pose to the second pose based on the change in the pose of the display device.

19 Claims, 8 Drawing Sheets

POSITIONING AN OBJECT BASED ON ALIGNED IMAGES OF THE OBJECT

FIELD OF THE INVENTION

This invention relates generally to a method for positioning an object, and more particularly to a method for positioning the object based on aligned images of the object.

BACKGROUND OF THE INVENTION

Radiotherapy

Radiotherapy directs high-energy ionizing radiation at unhealthy tissues, e.g., a tumor, in the body of a patient while sparing healthy tissue. One form of radiation therapy is particle beam therapy, where a depth of a maximum exposure can be controlled. However, location of the tumors, especially tumors near vital organs, such the brain, liver, lung, stomach and heart, needs to be determined precisely. Therefore, it is desired to position all tissue structures of the patient in accordance with a treatment plan.

Radiotherapy directs high-energy ionizing radiation at unhealthy tissues in the human body while sparing healthy tissue. One form of radiation therapy is particle beam therapy, where a depth of a maximum exposure can be controlled. However, unlike in the traditional photon-based radiotherapy, the peak of the dose is located inside the tissue, and the exact position of the peak dose in depth is determined by the energy and the tissues in the path of the particle beam. Therefore, the location of target tissue needs to be determined precisely. Therefore, it is desired to exactly position all tissue structures of the patient in accordance with the geometric alignment of the treatment beam specified in the treatment plan.

Radiotherapy uses ionizing radiation as part of cancer treatment to control malignant cells. It may be used for curative or adjuvant cancer treatment. It is used as palliative treatment, where a cure is not possible and the aim is for local disease control or symptomatic relief, or as therapeutic treatment, where the therapy has survival benefit and it can be curative. Radiotherapy is used for the treatment of malignant tumors, and may be used as the primary therapy. It is also common to combine radiotherapy with surgery, chemotherapy, hormone therapy or combinations thereof.

In oncological cases, the radiation therapy is commonly applied primarily to the tumor. The radiation fields may also include adjacent lymph nodes if the nodes are clinically involved with the tumor, or if there is thought to be a risk of metastasis. It is necessary to include a margin of normal tissue around the tumor to allow for uncertainties in the set-up of the patient, and internal tumor motion.

It should be noted, that radiotherapy is typically provided in short sessions over several weeks, e.g., three or four, to allow the patient to recover between treatments. Thus, identical set-ups are difficult to achieve. Therefore, the patient's skin is usually marked with indelible ink, during treatment planning, to indicate to the radiotherapist how to set-up the patient relative to the beam.

The uncertainties in the set-up can also be caused by internal movement, for example, respiration and bladder filling, and movement of external skin marks relative to the tumor location.

To spare normal tissues, such as skin or organs, through which radiation must pass in order to treat the tumor, shaped radiation beams are aimed from several angles of exposure to intersect at the tumor, providing a much larger absorbed dose at the tumor than in the surrounding, healthy tissue. Typically, the radiation source is placed on a gantry that rotates around the patient. The goal is to place the tumor at the iso-center of the central axis of the beam as the beam rotates, so that the beam always passes through the tumor, and much less frequently through healthy tissue.

Positioning a Patient

A common problem in radiation therapy is positioning the patient with respect to radiation equipment in accordance to the treatment plan. The treatment plan is typically developed using a high-resolution computer tomography (CT) scan, which contains three-dimensional (3D) volume data representing a density of the tissue. During the treatment, the patient needs to be positioned with respect to the radiation equipment to ensure that the tumor is positioned at the iso-center of the central axis of the radiation beam and thus that the planned radiation dose is delivered to the tumor.

To achieve this goal, a set of X-rays is usually acquired and compared to the expected view of the CT volume. The error in the positioning is estimated and the patient is moved to the correct position. Currently this positioning is performed either manually or semi-automatically.

The manual method is tedious and requires an understanding of 3D geometry of objects manipulated over six-degrees of freedom (6-DOF). The therapist moves a couch with the patient and takes X-ray images after each movement. This procedure might take a long time and expose the patient to a large dose of non-therapeutic X-ray radiation.

Automatic methods may position the patient incorrectly. Therefore, the radiotherapist needs to check the results of the automatic positioning. Furthermore, the necessity of manipulating rendered 3D volumes by the therapist, for setting an initial condition or marking point-correspondences using conventional input devices, such as mouse or trackball, are difficult and unintuitive for the following reasons.

The CT scan data form a 3D volume that needs to be manipulated with 6-DOF. Such manipulation is difficult using a 2D manipulator (mouse) and a 2D image.

With conventional user interfaces, the mouse and a display device are not co-located, which makes it difficult to identify correspondences.

SUMMARY OF THE INVENTION

The objective of the invention is to provide a system and a method for positioning an object based on images of the object.

One embodiment of the invention describes a method for positioning an object from a first pose to a second pose. The method displays concurrently a first image and a second image on a display device, wherein the first image and the second image represent respectively the first pose and the second pose of the object. The method updates, in response to a change in a pose of the display device, the second image such that an alignment of the first image and the second image on the display device depends on the change in the pose of the display device, and positions the object from the first pose to the second pose based on the change in the pose of the display device.

Another embodiment of the invention describes a system for positioning an object from a first pose to a second pose, comprising: a display device configured to display concurrently a first image and a second image, wherein the first image and the second image represent respectively the first pose and the second pose of the object; rendering engine configured to update, in response to a change in the pose of the display device, the second image such that an alignment of the first image and the second image on the display device depends on the change in the pose of the display device; and a positioning module configure to position the object from the first pose to the second pose based on the change in the pose of the display device.

DETAILED DESCRIPTION OF THE PREFERRED EMBODIMENT

Figure 1:
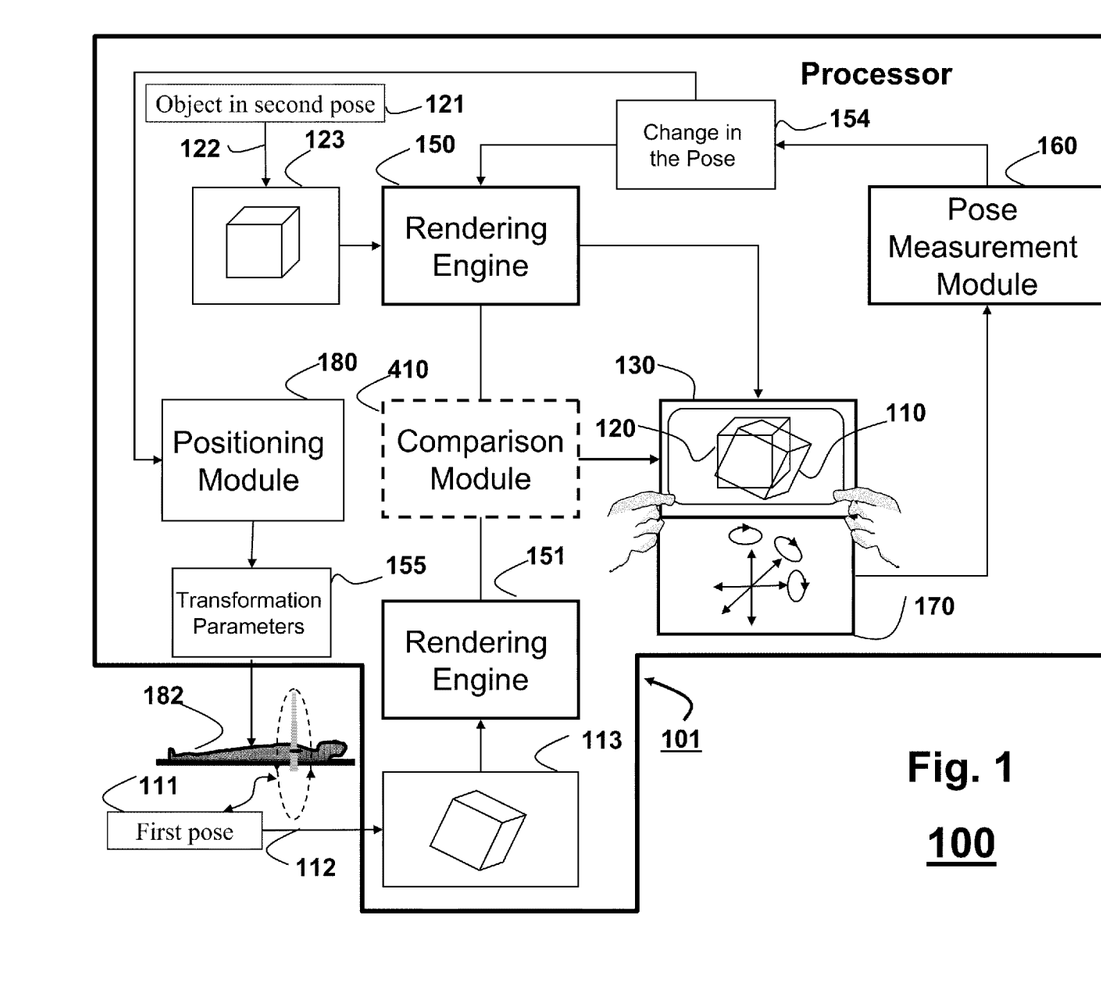
FIG. 1 is a block diagram of a method and a system for positioning an object according to an embodiment of an invention.

FIG. 1 shows a method and a system 100 for positioning an object from a first pose 111 to a second pose 121 according to embodiments of the invention. The method position the object based on an alignment of a first image 110 and a second image 120 on a display device 130. The first image and the second image represent respectively the first pose and the second pose of the object, and displayed on the display device concurrently. The method 100 is executed by a processor 101. The processor includes a memory for various models, input/output interfaces, and graphic processing unites (GPU) as known in the art.

The first image is rendered 151 from an image 111 acquired 112 from the object positioned in the first pose. The second image is rendered 150 from a volumetric image 123 acquired 122 from the object positioned in the second pose. In several embodiments the images are compared 410 as described below.

In some embodiments, the object is a patient 182 positioned for a treatment. In one embodiment, the volumetric image is constructed from a detailed computer tomography (CT) scan acquired of the patent during a treatment planning. In other embodiments, the volumetric image is acquired by magnetic resonance imaging (MRI) volume, and positron emission tomography (PET). The first image is constructed from an X-rays image acquired of the patient during set-up for a treatment session. It is understood, that the object can be any arbitrary object, and the patient is but one example object.

The pose of the object has a 3D location and a 3D orientation resulting in six degrees-of-freedom (6-DOF). The images are aligned by changing the pose of the display device. Typically, an operator move the display device with 6-DOF while aligning the second image with the first image. After the images are aligned, e.g., registered with each other, the change in the pose of the display device indicates a transformation, e.g., transformation parameters 155, for positioning 180 the object from the first pose to the second pose.

The idea behind the invention is high technology solution similar to a classic children's game. In the game, a tray has a target hole and a marble. You use your hands to maneuver the marble from its current position into the target hole. However, we do this in a non-intuitive way. We fix the marble in place at its current position, and instead maneuver the target hole to align with the marble. Also, we replace the tray with a zero-gravity display device, the hole and marble with translatable and rotatable images, optical encoders measure, and apply matrix transformations and distance metrics such as the Normalized Cross-Correlation, Kullback-Leibler divergence and others, to align the particle beam with the patient using two hands in a natural way.

Typically, the image 113 is two-dimensional (2D). Thus, a rendering engine 151 sends the image for displaying without a substantial change. However, the volumetric image 123 is three-dimensional (3D), and is converted to 2D by the rendering engine 150. The rendering engine 150 renders the second image from the volumetric image based on the change in the pose of the display devise 154 determined by a pose measurement module 160 in response to a motion of the display device. Because the second image is updated in response to the change in the pose of the display device, the alignment of the first image and the second image on the display device depends on the change in the pose of the display device.

Figure 2:
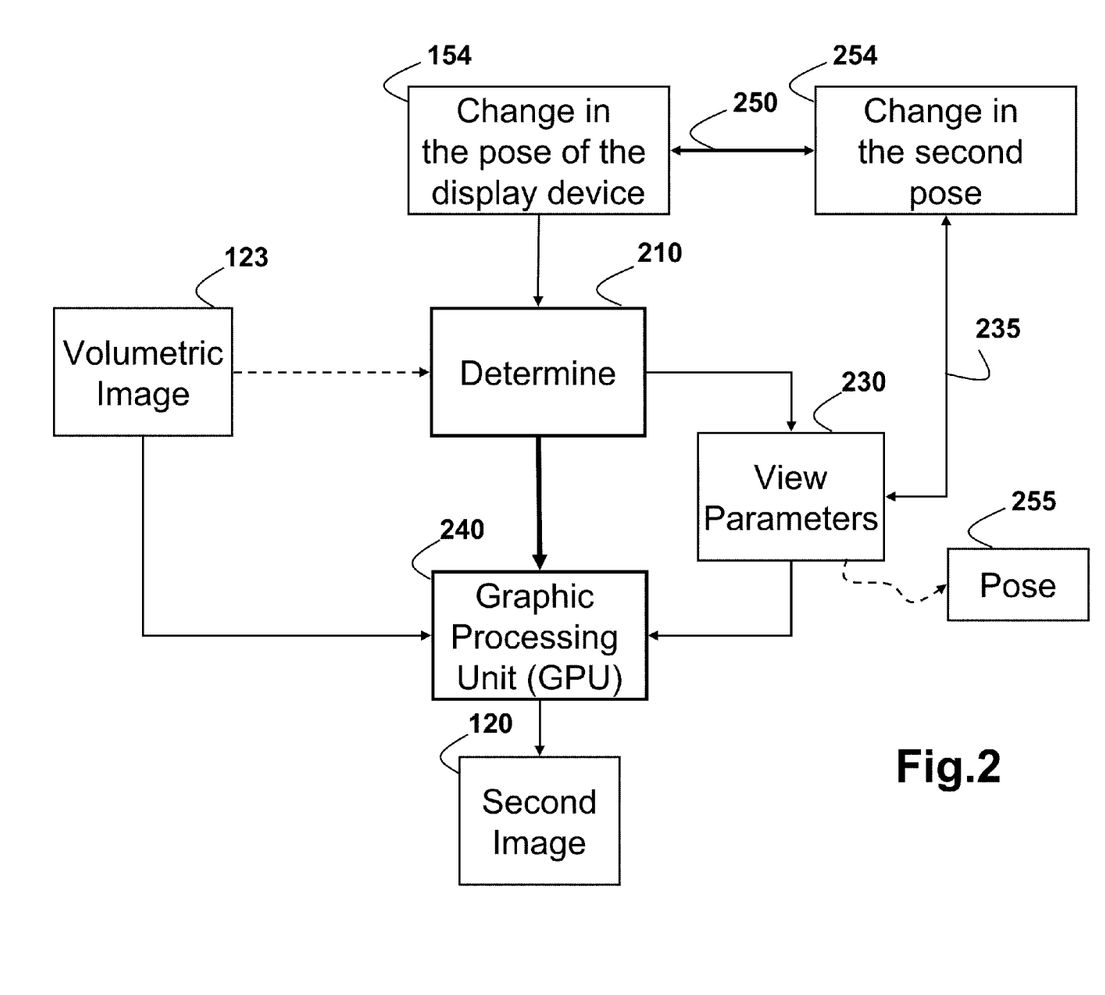
FIG. 2 is a block diagram of a method for displaying and updating a current data model according to an embodiment of the invention.

FIG. 2 shows the method for rendering the second image on the display device. Based on the change in the pose of the display devices 154, e.g., translation and rotation, the method determines 210 view parameters 230 representing 235 the object having a pose 255 resulted from a change in the second pose 254. The change in the second pose corresponds 250 to the change in the pose of the display device according to the embodiments of the invention. A graphic processing unit (GPU) 240 renders the second image from the volumetric image 123 according to the view parameters.

For example, in one embodiment, the second image 120 is a synthetic X-ray view, i.e., digitally reconstructed radiograph (DRR) image as it would have been acquired by an X-ray imager from the object having the pose 255.

Figure 3:
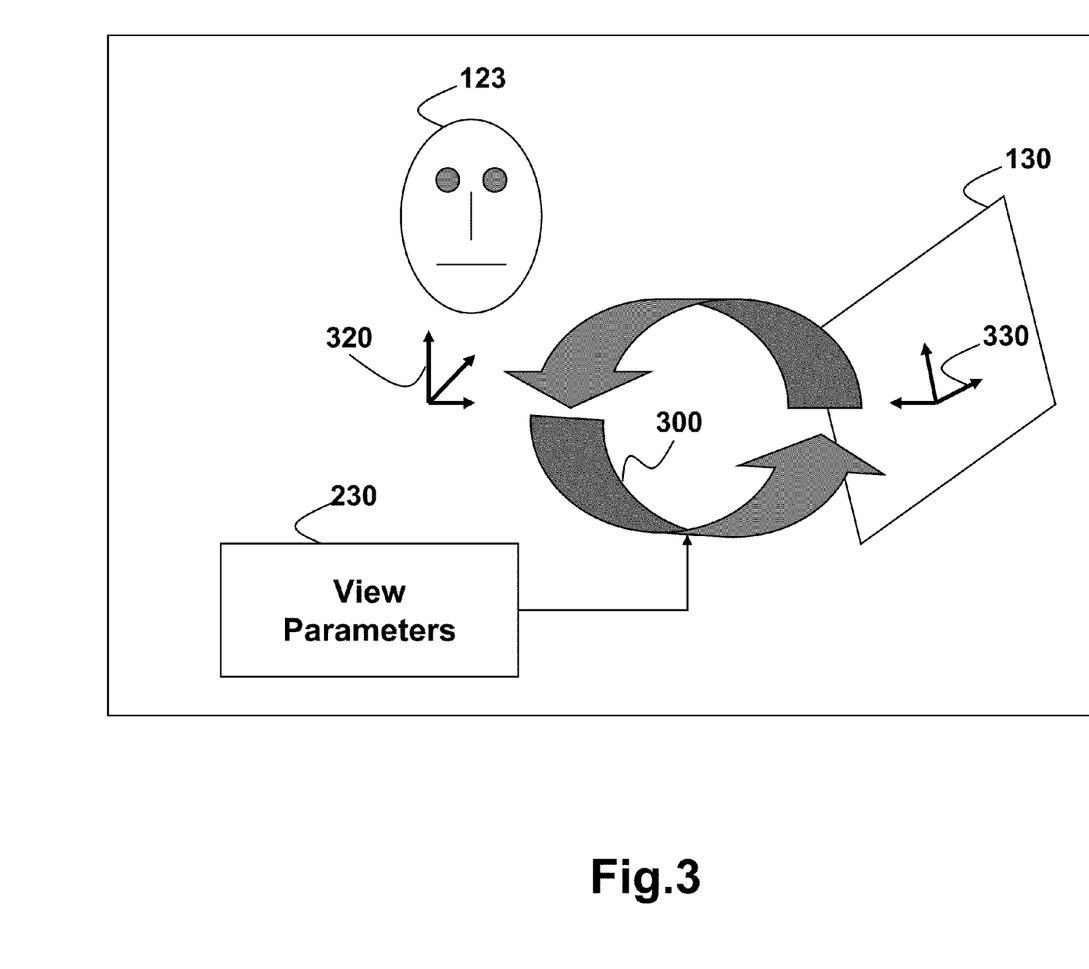
FIG. 3 is a block diagram of a method for coordinate transformations according to an embodiment of the invention.

FIG. 3 shows a coordinate transformations 300 performed by the rendering engine 150. The volumetric image 123 has an associated global coordinate system 320. The view parameters 230 are associated with an image coordinate system 330 of the display device. If the intrinsic and extrinsic parameters of the camera, e.g., the X-ray imager are known, e.g., focal length, and the location of the principal point in the image, then the parameters that need to be recovered are determined only by the change in the pose 154 of the display device 130.

The display device is rigidly arranged on a manipulator 170 having a 6-DOF. Accordingly, the display device can be moved with 6-DOF. The change of a pose of the manipulator, and indirectly that of the display device, is sensed by the pose measurement module 160. The change in the pose of the manipulator is described by transformation parameters 155. In one embodiment, we position 180 the patient 182 for radiation therapy based the transformation parameters after the first and the second images are aligned.

Comparison of Images

Figure 4:
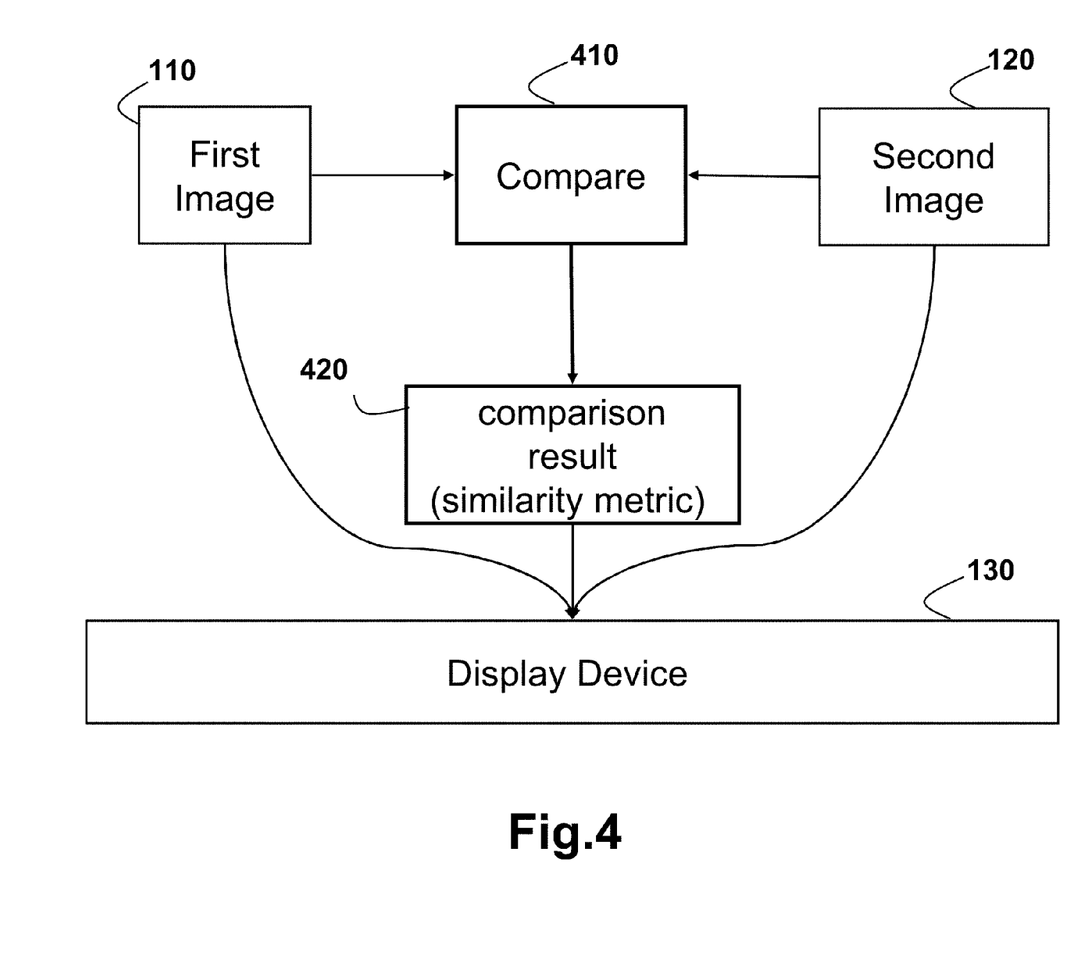
FIG. 4 is a block diagram of a method for comparison of data models according to an embodiment of the invention.

FIG. 4 shows the comparison module, which compares 410 the first and the second images to produce a comparison result 420 based on some similarity metric, e.g., Euclidean difference, Kullback-Leibler (KL) divergence, Normalized Cross-Correlation.

The first and the second image may be misaligned when first displayed. The objective of the alignment process is to align the images with each other by moving the display device. The movement of the display device is typically performed by an operator. To facilitate the alignment, some embodiments render the comparison result, e.g., a direction and/or a size of misalignment, on the display device. In one embodiment, the misalignment is highlighted on the display.

In another embodiment, the value of the comparison result is displayed. In yet another embodiment, an expanding bar indicative of the misalignment is displayed on a side of the display device.

N-DOF

During the positioning of the object, the 6-DOF corresponds to, e.g., three rotations and three translations, i.e., rigid transformation. However, in some embodiments, the volumetric image 123 is taken several weeks apart from the image 113, and the image 113 reflects a non-rigid deformation. For example, the alignment of soft tissues might require some fine local stretching and pushing of the tissues, intestines may have gas, kidneys may move, and lungs may be at a different inflation level. Accordingly, in one embodiment, the display device 130 includes a touch sensitive screen. Thus, the embodiment allows for rigid transformation by moving the display device and for non-rigid correction by manipulating the images using the touch sensitive screen.

Horizontal Manipulator

Figure 5:
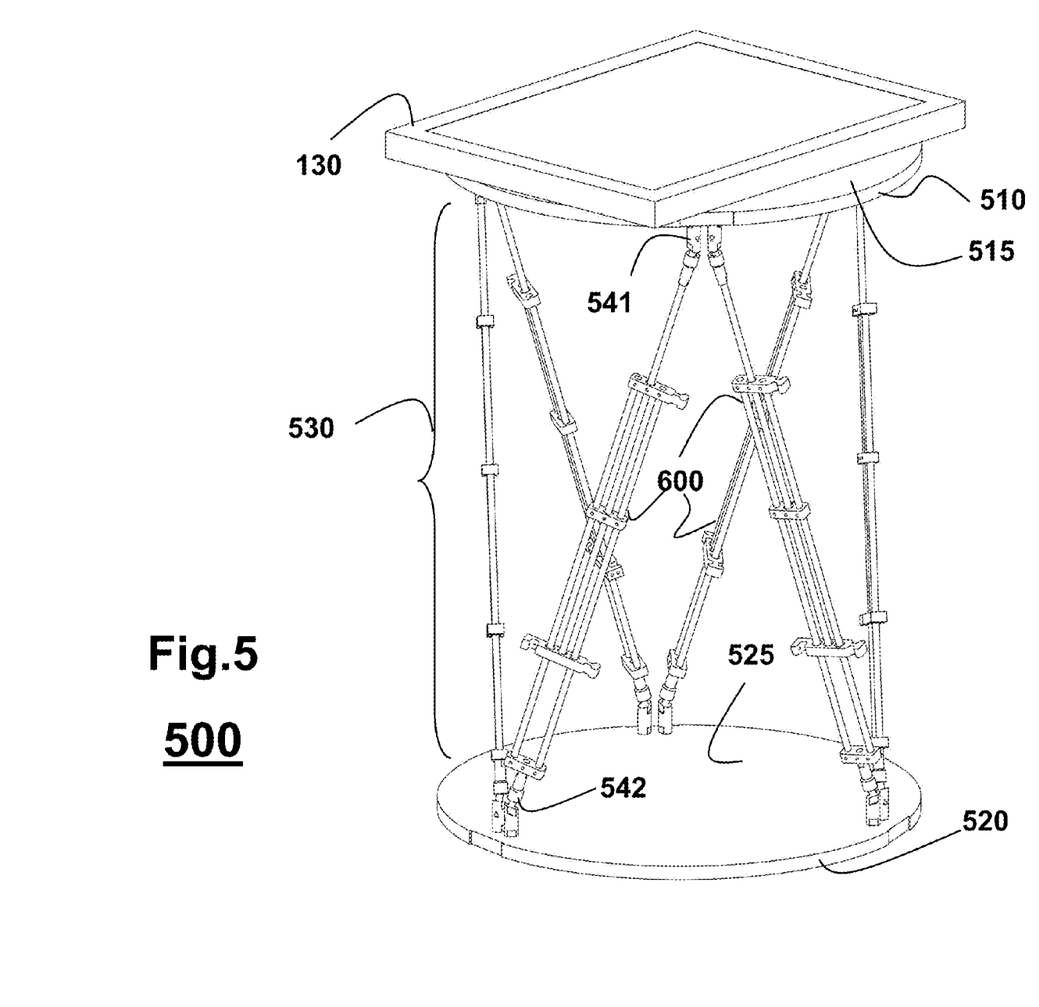
FIGS. 5-7 are schematic of different views of a horizontal manipulator according to an embodiment of the invention.

FIG. 5 shows the display device, and a horizontal manipulator 500, which includes a modified hexapod, Hayward et al., "Kinematic Decoupling In Mechanisms And Application To A Passive Hand Controller. J. Robotics Systems," Wiley, Vol. 10, No. 5, pp. 767-790, 1993.

The manipulator 500 enables the 6-DOF manipulation of the display device. The manipulator includes an upper platform 510 and a lower platform 520, each platform having opposed upper 515 and lower surfaces 525. The lower surface of the upper platform is generally aligned with and spaced from the upper surface of the lower platform.

Figure 6:
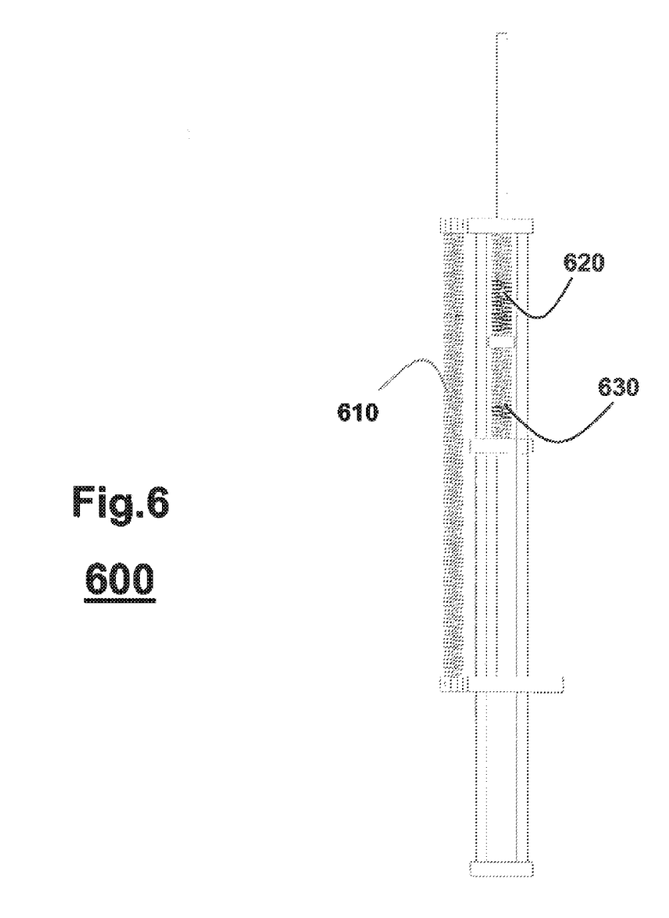

The manipulator further includes a suspension mechanism 530 to provide zero-gravity suspension for the display device. The suspension is implemented using a system of leg assembly 600 shown in FIG. 6. The leg assembly includes a long "anti-gravity" spring 610 for compensating a weight of the display device. The leg assembly further includes two springs, i.e., an extension compensation string 620 and a compression compensation string 630, for re-centering the suspension mechanism 530 when the upper platform is released. Two freely swiveling ball joints 541 and 542 connect the leg assembly to the platforms. In one embodiment, the suspension mechanism includes six independent leg assemblies extending between the platforms.

In one embodiment, the upper surface 515 of the upper platform 510 serves as a display platform to be rigidly connected with the display device 130. In another embodiment, the display platform is the lower surface of the lower platform.

The suspension mechanism 530 allows for a 6-DOF positioning of the display platform. Force needed to displace the display device along any of the degrees of freedom is proportional to the extension of the leg assembly, see Hayward et al. for further details.

Figure 7:
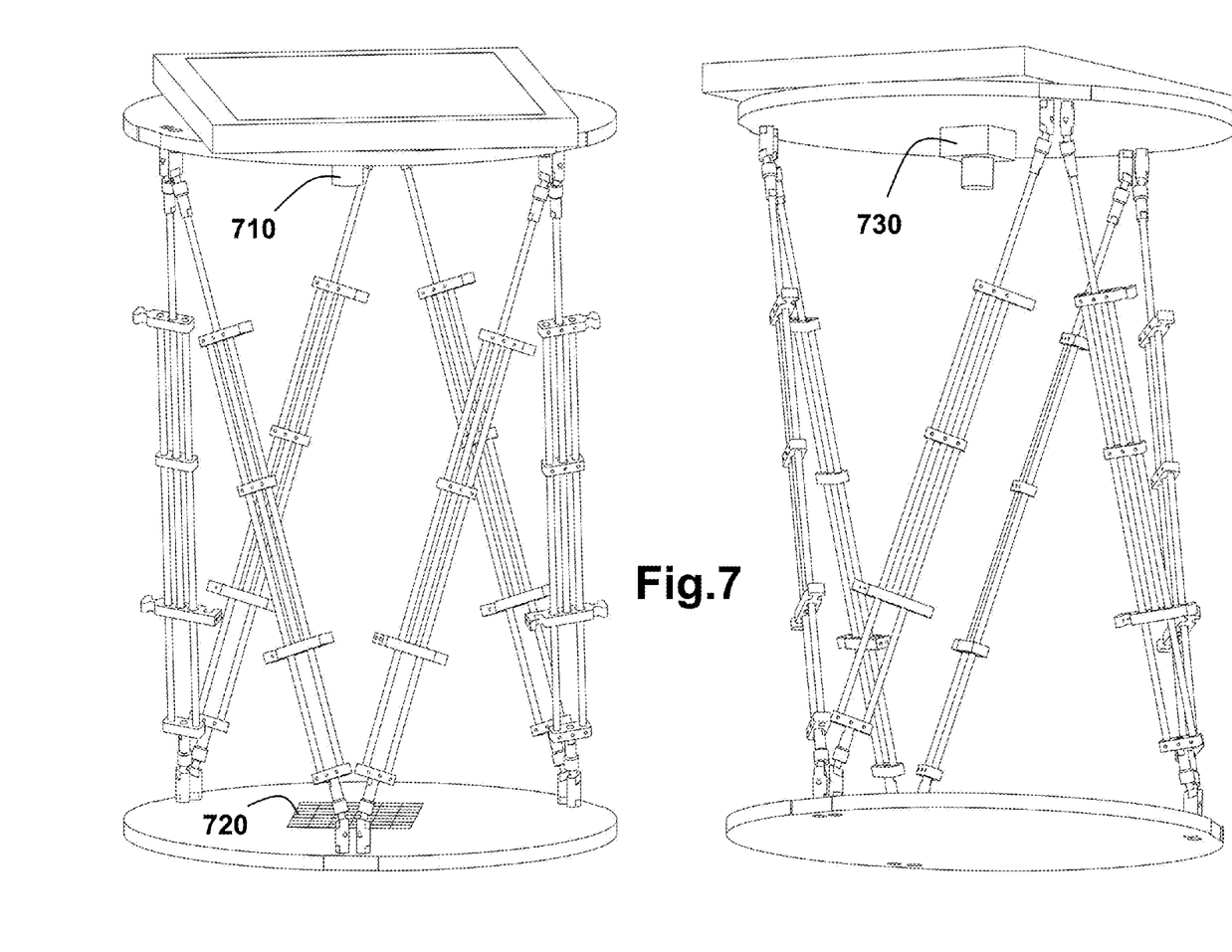

As shown on FIG. 7, the pose measurement module includes a camera 710 connected to one platform, and a calibration pattern 720 on the other platform. For example, in one embodiment, the camera is connected to the upper platform, and the calibration pattern is connected to the lower platform. It should be noted that the pattern and camera can be reversed. The only thing that matters is that one is stationary, and the other free to move. In another embodiment, the calibration pattern has a checkerboard pattern.

A pose detector 730 determines the pose of the camera based on images of the calibration pattern acquired by the camera. In one embodiment, the pose detector is running on a processor of the camera. In another embodiment, the calibration pattern is backlit by a lamp and a diffuser commonly used in liquid crystal displays (LCDs), so the manipulator 500 can be used in dimly lit environments, e.g., the treatment room.

The images of the calibration pattern are used to determine the homographic transformation between the global and image coordinate systems, i.e., the transformation parameters 155. Example of determining the transformation parameters using computer vision-based estimation is described in U.S. Pat. No. 6,527,395, incorporated herein by reference.

Vertical Manipulator

Figure 8:
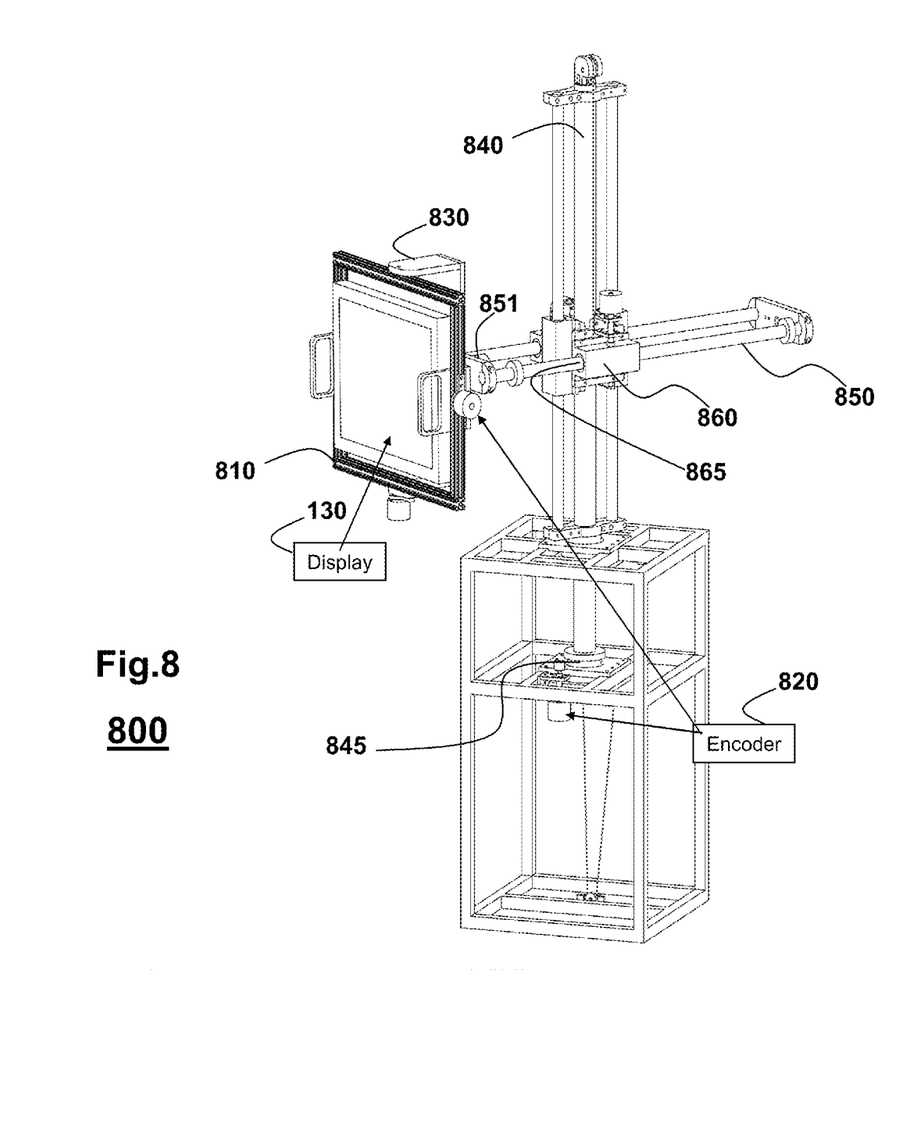
FIG. 8 is a schematic view of a vertical manipulator according to an embodiment of the invention.

FIG. 8 shows a vertical manipulator with increased range of motion, vertical display, direct mapping of forces to the DOF variables, and absence of a central "attractor", i.e., the position to which the system returns when no forces are applied.

The vertical manipulator 800 includes a display platform 810 connected to the manipulation device for 6-DOF manipulation. Pose measurement module includes a rotational optical encoder 820. Vertical and in-out displacements are encoded by a rotating wheel with a cable attachment. This motion is sensed as a composition of two rotations and an in-out displacement. Note the absence of the lateral linear displacement sensor. From the set of six calibrated rotation measurements, we calculate the transformation parameters by propagating the rotations along a kinematic chain.

The vertical manipulator includes a gimbal assembly 830 with 3-DOF connected to the display platform, and a central column 840 oriented vertically. The vertical manipulator further includes a swinging arm 850 connecting 851 the gimbal assembly with the central column. The swinging arm is adapted to rotate around the central column, to slide up and down on the central column in a vertical direction, and extend or retract in a horizontal direction.

In one embodiment, the swinging arm is connected to a carrier 860 and is configured to slide in horizontal direction through an opening 865. In turn, the carrier is positioned around the central column enabling the swinging arm to slide in vertical direction.

In one embodiment, the display platform has four rotations and two translations, not directly corresponding to the target three rotations and three translations system. In this embodiment, the lateral translation of the display platform is achieved by rotation around the central column 845, an outward extension of the swinging arm, and the gimbal rotation around a vertical axis in the direction opposite to the rotation 845.

In one embodiment, the vertical displacement requires about 60 kilos of constant load. Since the load does not change, due to the decoupling and elimination of cantilever effect of the swinging arm, only a static compensation is necessary by a static weight to counterbalance the swinging arm and the gimbal assembly.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

We claim:

1. A method for positioning an object from a first pose to a second pose, comprising a processor for performing steps of the method, comprising the steps of:

displaying concurrently a first image and a second image on a display device, wherein the first image and the second image represent respectively the first pose and the second pose of the object;

updating, in response to a change in a pose of the display device, the second image such that an alignment of the first image and the second image on the display device depends on the change in the pose of the display device; and positioning the object from the first pose to the second pose based on the change in the pose of the display device.

2. The method of claim 1, further comprising:
rendering the first image from an image acquired of the object having the first pose; and
rendering the second image from a volumetric image acquired of the object having the second pose.

3. The method of claim 2, wherein the updating further comprising:
determining the change in the pose of the display device;
determining view parameters representing the object having a pose resulted from a change in the second pose, wherein the change in the second pose corresponds to the change in the pose of the display device; and
rendering the second image from the volumetric image according to the view parameters.

4. The method of claim 2, wherein the object is a patient positioned for a treatment, and the first image is rendered from an X-ray image acquired of the patient.

5. The method of claim 4, wherein the volumetric image is constructed from volumetric data acquired of the patient using computer tomography (CT), magnetic resonance imaging (MRI), or positron emission tomography (PET).

6. The method of claim 1, further comprising:
registering the second image with the first image on the display device based on the change of the pose of the display device.

7. The method of claim 1, further comprising:
determining transformation parameters suitable for the positioning of the object based on the change in the pose of the display device.

8. The method of claim 7, wherein the display device includes a touch sensitive screen, and the first image and the second image are suitable for being manipulated on the display device using the touch sensitive screen, further comprising:
correcting the transformation parameters based on the manipulation of the first image and the second image on the display device.

9. The method of claim 1, further comprising:
comparing the first image and the second image to produce a comparison result; and
displaying the comparison result on the display device.

10. The method of claim 9, wherein the comparison result is indicative of a direction of misalignment.

11. The method of claim 9, wherein the comparison result is a similarity metric.

12. The method of claim 1, further comprising:
arranging rigidly the display device on a manipulator having a six-degrees of freedom (6-DOF), such that the display device has 6-DOF, wherein the manipulator includes a suspension mechanism configured to provide zero-gravity suspension for the display device.

13. A system for positioning an object from a first pose to a second pose, comprising:
a display device configured to display concurrently a first image and a second image, wherein the first image and the second image represent respectively the first pose and the second pose of the object;
rendering engine configured to update, in response to a change in the pose of the display device, the second image such that an alignment of the first image and the second image on the display device depends on the change in the pose of the display device; and
a positioning module configured to position the object from the first pose to the second pose based on the change in the pose of the display device.

14. The system of claim 13, further comprising:
a touch sensitive screen mounted on the display device such that the second image is suitable to be manipulated on the display device using the touch sensitive screen;
means for determining transformation parameters based on the pose of the display device; and
means for correcting the transformation parameters based on the manipulation of the second image using the touch sensitive screen.

15. The system of claim 13, further comprising:
a camera connected to the display device such that the change in the pose of the display device determines a change in a pose of the camera;
a calibration pattern positioned in a focus of the camera; and
a pose measurement module configured to determine the change in the pose of the camera based on an image of the calibration pattern acquired by the camera.

16. The system of claim 13, further comprising:
a manipulator having six degrees of freedom (6-DOF) rigidly connected to the display device.

17. The system of claim 16, wherein the manipulator is configured to provide a zero-gravity suspension for the display device.

18. A system for positioning an object from a first pose to a second pose, comprising:
a manipulator having six degrees of freedom (6-DOF) configured to be rigidly connected to a display device, wherein the display device is configured to display concurrently a first image and a second image, wherein the first image and the second image represent respectively the first pose and the second pose of the object;
rendering engine configured to update, in response to a change in the pose of the manipulator, the second image such that an alignment of the first image and the second image on the display device depends on the change in the pose of the manipulator; and
a positioning module configured to determine the change in the pose of the manipulator, wherein the object is suitable to be positioned from the first pose to the second pose based on the change in the pose of the manipulator.

19. The system of claim 18, further comprising:
means for determining view parameters representing the object having a pose resulted from a change in the second pose, wherein the change in the second pose corresponds to the change in the pose of the manipulator; and
a graphic processing unit configured to render the second image from a volumetric image according to the view parameters.

* * * * *